United States Patent
Mackenzie et al.

(10) Patent No.: US 10,900,892 B1
(45) Date of Patent: Jan. 26, 2021

(54) VALIDATION OF SENSOR CALIBRATION

(71) Applicant: SciLogica Corp., Denver, CO (US)

(72) Inventors: Alasdair Allan Mackenzie, Herefordshire (GB); Barry Colin Crane, Oxon (GB); Nicholas Paul Barwell, Warwickshire (GB); Praveen Sagar, Bucks (GB); Robert Perkins, Oxfordshire (GB)

(73) Assignee: SciLogica Corp., Denver, CO (US)

(*) Notice: Subject to any disclaimer, the term of this patent is extended or adjusted under 35 U.S.C. 154(b) by 0 days.

(21) Appl. No.: 16/792,458

(22) Filed: Feb. 17, 2020

(51) Int. Cl.
| | |
|---|---|
| *G01N 21/00* | (2006.01) |
| *G01N 21/31* | (2006.01) |
| *G01N 21/64* | (2006.01) |
| *G01N 33/49* | (2006.01) |

(52) U.S. Cl.
CPC ......... *G01N 21/31* (2013.01); *G01N 21/6486* (2013.01); *G01N 33/49* (2013.01); *G01N 2201/062* (2013.01); *G01N 2201/0612* (2013.01)

(58) Field of Classification Search
CPC ............... G01N 21/31; G01N 21/3103; G01N 2021/3125; G01N 2021/3148; G01N 33/49; G01N 21/6486; G01N 1/10; G01N 21/00
See application file for complete search history.

(56) References Cited

U.S. PATENT DOCUMENTS

| | | | |
|---|---|---|---|
| 2006/0213838 A1* | 9/2006 | Iwata | G01N 21/31 |
| | | | 210/656 |
| 2012/0142115 A1 | 6/2012 | Banks et al. | |

FOREIGN PATENT DOCUMENTS

| | | |
|---|---|---|
| EP | 2888999 A1 | 7/2015 |
| EP | 2912992 A1 | 9/2015 |
| JP | H03102245 A | 4/1991 |
| WO | WO-2017/142399 A1 | 8/2017 |
| WO | WO-2020/005823 A1 | 1/2020 |

OTHER PUBLICATIONS

Ge et al., "High-stability non-invasive autoclavable naked optical CO2 sensor", Biosensors and Bioelectronics, 15 2003:18:857-865.
(Continued)

*Primary Examiner* — Abdullah Nur
(74) *Attorney, Agent, or Firm* — Harness, Dickey & Pierce, P.L.C.

(57) ABSTRACT

There is provided a method of validating a calibration of a sensor represented by a calibrated relationship between concentration of an analyte in a sample and measurements from a sensor of an optical property of a sensing substance, wherein the optical property of the sensing substance has a spectrum that varies with the concentration of the analyte in the sample, and the spectrum has an isosbestic wavelength at which the optical property does not vary with concentration of the analyte, the method comprising making measurements of the optical property at three or more wavelengths of light while the sensing substance is exposed to the sample, determining whether the measurements of the optical property are inconsistent with the calibrated relationship, and outputting a warning signal in response to the measurements of the optical property being inconsistent with the calibrated relationship.

21 Claims, 9 Drawing Sheets

(56) References Cited

OTHER PUBLICATIONS

Ge et al., "Study on low-cost calibration-free pH sensing with disposable optical sensors", Analytica Chimica 5 Acta, 2012:734:79-87.
Rovati et al, "Plastic Optical Fiber pH Sensor Using a Sol-Gel Sensing Matrix", MOH YASIN Sulaiman W. Harun and Hamzah AROF, eds. Fiber Optic Sensors.
Phillips et al., "Carbohydrate sensing using a fluorescent molecular tweezer", Chem. Commun., 2009, 6557-6559.
Review on Recent Developments of Fluorescent Oxygen and Carbon Dioxide Optical Fiber Sensors, Photonic Sensors, 2011, 1, 234-250.
Pittman et al., "A new method for the measurement of percent oxyhemoglobin" Journal of applied physiology, vol. 38, No. 2, Feb. 1975, pp. 315-320.
European Search Report regarding EP 20165005.8, dated Sep. 22, 2020.

* cited by examiner

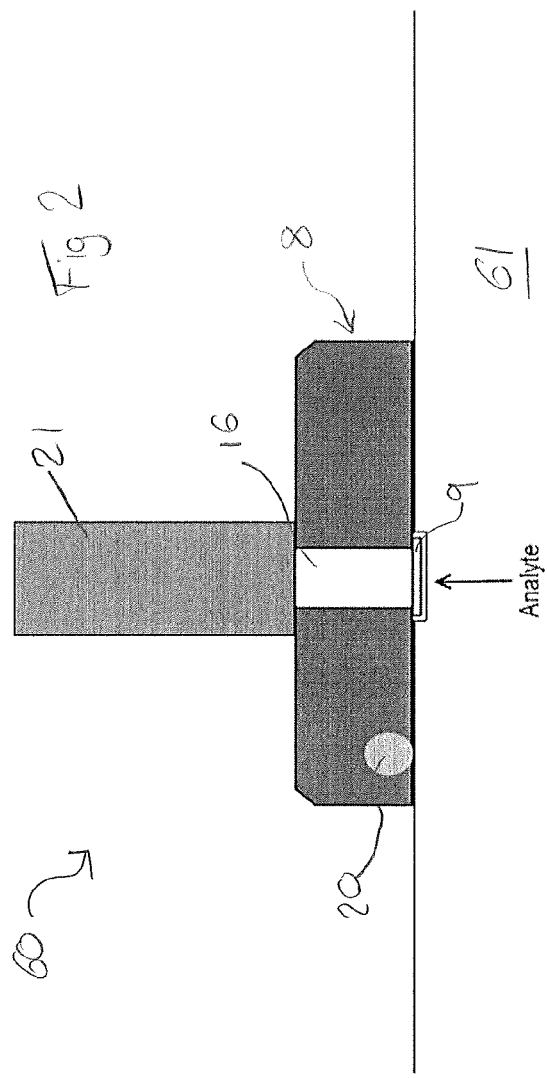

VALIDATION OF SENSOR CALIBRATION

FIELD

The present invention relates to methods for validating a calibration of a sensor. In particular, it relates to validating the calibration of a sensor which measures an optical property of a sensing substance.

BACKGROUND

It is desirable in many areas to be able to determine the concentration of a particular analyte in an environment which may contain a mixture of several different substances, both gaseous and non-gaseous. For example, in some clinical settings, such as dialysis treatment or monitoring of patients in intensive care, it is important to be able to accurately determine the concentration of carbon dioxide or ions such as potassium or sodium in a patient's blood in real-time, and the provision of continuous real-time measurement data to a clinician in acute care settings is often invaluable as a means of guiding the administration of therapies. Another example is the monitoring of controlled environments in the food industry, where the presence of oxygen or contaminant gases may be undesirable due to the risk of causing spoilage of food.

One known type of sensor uses a luminescent compound, for example a fluorescent organic dye, with a luminescence having a characteristic that depends on the concentration of the target analyte. By exciting the luminescent compound and measuring its luminescence while it is exposed to a sample containing the analyte, the concentration of the analyte in the sample can be determined. This type of sensor has the advantage that it can be operated continuously, so does not require taking regular samples, for example of blood or the atmosphere in which food is stored, for analysis or other similarly inconvenient procedures. Other systems may measure the transmission of light by a sensing substance, and use this to determine the concentration of the analyte in the sample.

However, the values of the analyte concentration reported by sensors are prone to error. Spectrophotometric and fluorometric instrumentation has advanced over the past 50 years, and many of the variables that generated analytical errors in earlier days have been reduced. These errors were generally caused by instrument drift from light sources, detectors, and electronic noise within the detection system. Double beam spectrophotometry and fluorimetry, where a blank sample with no detection chemistry automatically references out any absorption or fluorescence interferences from the analysis, has also reduced the error in many measurements. However, some of these types of system can be cumbersome and expensive to maintain and operate.

The advent of inexpensive fibre optic devices has again highlighted the need for signal stability, since many of these devices, particularly those aimed at the invasive or semi-invasive continuous measurement of analytes in critically-ill patients, are used over prolonged periods of time. In these cases, a low level of drift can, over many hours, result in very inaccurate measurements. The drift in these fibre optic systems is often attributable to drift in the intensity or wavelength of light from light sources, such as LEDs or laser diodes, drift in the sensitivity of detection systems, and photobleaching of the detection chemistries. Although some techniques have been developed to reduce drift, values reported by the sensors can still drift over long times.

In particular, it is presently difficult to establish whether the values of concentration reported by the sensor have drifted or not, and by how far. If the sensor provides erroneous data unbeknownst to the operator, then making a therapeutic decision based on this data can be dangerous to the patient. In order to avoid this, sensor apparatuses may require periodic recalibration of the sensor at time intervals based on estimated values of drift. These time intervals are likely to be chosen conservatively, and lead to an undue burden on operators who have to frequently recalibrate their sensors. Additionally, there is no guarantee that values have not drifted faster than expected between calibrations.

Therefore, there is a need for a method of validating the values reported by a sensor, in order to provide clinicians and other operators with confidence that the values reported can be relied upon, and to indicate when recalibration is required.

SUMMARY

According to a first aspect of the invention, there is provided a method of validating a calibration of a sensor represented by a calibrated relationship between concentration of an analyte in a sample and measurements from a sensor of an optical property of a sensing substance, wherein the optical property of the sensing substance has a spectrum that varies with the concentration of the analyte in the sample, and the spectrum has an isosbestic wavelength at which the optical property does not vary with concentration of the analyte, the method comprising making measurements of the optical property at three or more wavelengths of light while the sensing substance is exposed to the sample, determining whether the measurements of the optical property are inconsistent with the calibrated relationship, and outputting a warning signal in response to the measurements of the optical property being inconsistent with the calibrated relationship.

By making three or more measurements of a spectrum having an isosbestic wavelength, it can be determined whether the measurements are consistent with a prior calibrated relationship. The calibrated relationship may be thought as defining a surface in a three-dimensional space, where the dimensions of the space are the three measurements at different wavelengths. Points on the surface represent combinations of the three values which are consistent with the calibrated relationship. Therefore, it can be determined whether the measurements are consistent with the calibrated relationship by determining whether the measurements of the optical property define a point in this space which lies on (or sufficiently close to) a point on the surface defined by the calibrated relationship. Having three measurements allows the method to detect drift or error that affects all wavelengths equally, as well as drift that affects different wavelengths differently. By outputting a warning signal when the calibration is determined to be invalid, the burden on the operator is reduced, because recalibrations are only performed when measurements are actually at risk of being invalid. Further, the operator is given confidence that measurements are valid if no warning is provided.

In an embodiment, the method further comprises deriving a measure of concentration of the analyte in the sample from the measurements in accordance with the calibrated relationship. A determination of concentration is likely to be needed for reporting to the operator, and so calculating it as part of the validation process means that the measure of concentration can be used for validating the calibration, and it is not necessary to separately relate the calibration to raw measurement values for validation purposes.

In an embodiment, the calibrated relationship comprises a relationship between the concentration and a ratio between measurements of the optical property at a pair of wavelengths, and the step of deriving the measure of concentration comprises calculating a ratio between the measurements of the optical property at the two wavelengths and deriving the measure of concentration from the ratio in accordance with the calibrated relationship. Using a ratio between two measurements is advantageous, because it can compensate for certain common sources of error that affect measurements at all wavelengths by a multiplicative factor.

In an embodiment, the plurality of measures of concentration comprises a measure calculated using a ratio between two measurements of the optical property not made at the isosbestic wavelength. Because the measurement at the isosbestic wavelength does not vary with concentration, using a ratio of measurements away from the isosbestic wavelength can improve the contrast between the ratio calculated at different concentrations of the analyte.

In an embodiment, the method further comprises determining a measure of deviation of the measurements of the optical property from the calibrated relationship, and determining that the measurements of the optical property are inconsistent with the calibrated relationship if the measure of deviation is above a predetermined threshold. A measure of deviation provides a clear indication of the level of drift from the calibrated relationship, and can be used to set a well-defined and appropriate level at which the method should output a warning.

In an embodiment, the method further comprises deriving a plurality of measures of concentration of the analyte in the sample from the measurements at different wavelengths in accordance with the calibrated relationship, wherein the measure of deviation is a measure of variation between the plurality of measures of concentration. Using three measurements, a plurality of measures of concentration can be determined using different ones or combinations of the measurements. If these measures of concentration are not consistent, this is a clear indication that the calibrated relationship is no longer valid.

In an embodiment, the calibrated relationship comprises a relationship between the concentration and plural ratios between measurements of the optical property at respective pairs of wavelengths, and the step of deriving a plurality of measures of concentration of the analyte in the sample comprises calculating ratios between the measurements of the optical property at the respective pairs of wavelengths and deriving the plural measures of concentration from the ratios in accordance with the calibrated relationship. As mentioned above, ratios allow for the elimination of some types of common sensor error. If the ratios become inconsistent, this allows the method to detect that other types of error have become large enough to invalidate the measurement.

In an embodiment, the measure of variance is a coefficient of variation. This is a convenient technique for providing a measure of the variation of a set of values that is comparable with that of other sets of values, even when the absolute magnitudes are substantially different.

In an embodiment, one of the three or more wavelengths is the isosbestic wavelength. Measuring directly at the isosbestic wavelength allows certain types of error to be more easily detected, because the value of measurements at the isosbestic wavelength should not change with concentration, and changes are therefore indicative of error.

In an embodiment, one of the three or more wavelengths is a wavelength at which the spectrum of the optical property of the sensing substance has a maximum or a minimum. This will provide the greatest contrast between measurements at different concentrations, thereby increasing the sensitivity and reliability of measurements.

In an embodiment, the optical property is one of absorption and emission, and the spectrum is respectively one of an absorption spectrum and an emission spectrum. Absorption and emission spectra are convenient choices for optical properties to measure because they can be measured without the need for angle-resolved measurements or other complex measurement techniques.

In an embodiment, the optical property is emission, and making measurements of the optical property at three or more different wavelengths comprises for each one of the three or more wavelengths exciting the sensing substance using light of a first wavelength, and measuring the intensity of light emitted by the sensing substance at the one of the three or more different wavelengths, wherein the first wavelength is the same for each of the three or more wavelengths. This measurement scheme only requires light of a single wavelength to be generated by the apparatus and transmitted to the sensing substance, thereby simplifying the arrangement of light emitters needed in the apparatus. It is most appropriate where the sensing substance has a single excitation band, but emits at multiple wavelengths.

In an embodiment, the optical property is absorption, and making a plurality of measurements of the optical property at three or more different wavelengths comprises for each one of the three or more wavelengths exciting the sensing substance using light at the one of the three or more wavelengths, measuring the intensity of light emitted by the sensing substance at a second wavelength, wherein the second wavelength is the same for each of the three or more wavelengths. This measurement scheme only requires a single detector, because light is emitted at the same wavelength for different excitation wavelengths. It is most appropriate where the sensing substance can be excited in multiple different excitation bands, but emits at a single wavelength.

In an embodiment, the optical property is absorption, and making a plurality of measurements of the optical property at three or more different wavelengths comprises for each one of the three or more wavelengths illuminating the sensing substance using light at the one of the three or more wavelengths, measuring the intensity of light transmitted by the sensing substance at the one of the three or more wavelengths. This measurement scheme would also only require a single detector, and would also be advantageous in physical configurations where capturing emitted light from the sensing substance is challenging.

In an embodiment, the sensing substance comprises two species in equilibrium, the equilibrium between the two species being dependent on the concentration of the analyte in the sample. The two species in equilibrium can give rise to an isosbestic point in the spectrum of the sensing substance and the differing optical characteristics of the two species allow the detection of changes to the concentration of the analyte.

In an embodiment, the analyte is one of carbon dioxide, and hydrogen ions. These are analytes that are particularly desirable to measure in biological or clinical implementations, and where having confidence in the validity of the measurement can be critical to patient care.

In an embodiment, the sample comprises blood. Blood is a commonly sampled medium in clinical settings and is reflective of the levels of many important substances in the body.

In an embodiment, the sensing substance comprises 8-hydroxypyrene-1,3,6-trisulfonic acid. This is a readily-available, pH-sensitive dye that allows for the detection of carbon dioxide concentration in blood.

In an embodiment, making the measurements of the optical property comprises making raw measurements at a plurality of times and time-averaging the raw measurements. Time-averaging can reduce the sensitivity of the method to transient fluctuation in the measurements that are not indicative of the type of long-term drift that the method is primarily designed to detect. This reduces the incidence of false warnings. In an embodiment, the method further comprises an initial calibration step of determining the calibrated relationship between the concentration of the analyte and the measurements of the optical property. The initial calibration provides a baseline against which to compare later measurements, and confidence in the initial validity of the calibration of the sensor apparatus.

DRAWINGS

Embodiments of the present invention will now be described by way of non-limitative example with reference to the accompanying drawings, in which:

FIG. 2 is a schematic of a possible configuration of a sensor probe for extracorporeal measurement of analyte concentration in blood;

DETAILED DESCRIPTION OF EMBODIMENTS

Figure 1:
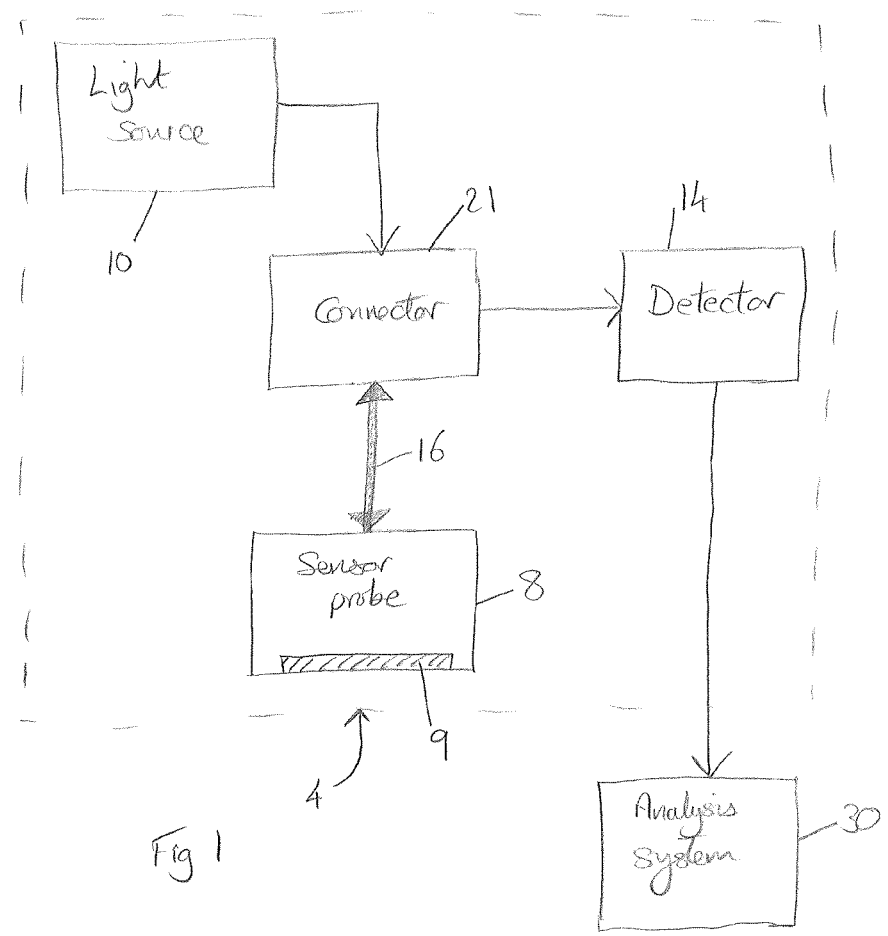
FIG. 1 is a schematic of a sensor apparatus in which the present invention may be implemented.

The present disclosure provides a method of validating a calibration of a sensor. FIG. 1 shows a sensor apparatus of the type in which the methods disclosed herein could be used. An example of such a sensor 4 may be a pH sensor for sensing carbon dioxide concentrations. The sensor apparatus comprises a sensor 4 comprising a sensing substance 9, and an analysis system 30.

The sensor 4 comprises a light source 10 configured to emit light that is used to measure an optical property of the sensing substance 9. For example, where the sensing substance 9 is a luminescent compound, the light source 10 may be any light source capable of emitting light at the wavelengths and intensities required to excite the luminescent compound. For example, the light source 10 may comprise a laser diode or an LED. The light source 10 may be a continuous light source, a light source with oscillating intensity, or a pulsed light source.

The sensor 4 further comprises a detector 14 configured to detect light received from the sensing substance. The detector 14 may be any device capable of producing a signal in response to receiving light at the wavelengths emitted by the sensing substance 9. For example, the detector 14 may comprise a charge-coupled device, an active-pixel sensor, a photodiode, or photoresistor. The signal output by the detector 14 may represent the intensity of light received from the sensing substance 9.

The sensor 4 comprises an optical fibre 16, arranged to guide light to and from the sensing substance 9. Optical fibres use total internal reflection to prevent light being lost from the fibre. This means light can be efficiently carried to and from the sensing substance, improving the signal and providing for higher-quality and more reliable measurements. They can also be made small and flexible, so are particularly suitable for sensors that must be inserted into the body of a patient. For example, the optical fibre 16 may comprise a PMMA fibre optic. The optical fibre 16 functions as an optical waveguide and any other suitable optical waveguide may be used in place of the optical fibre 16, when appropriate.

The sensor 4 comprises a sensor probe 8 in which the sensing substance 9 is provided. The sensor probe 8 may be the component of the sensor 4 which is directly exposed to the sample. In an embodiment, the sample comprises blood. The sensor 4 further comprises a connector 21 configured to connect the sensor probe 8 to the light source 10 and the detector 14. Some or all of the sensor 4 may be disposable. This is convenient in clinical contexts, where the sensor 4 is used to measure analyte concentrations inside the body of a patient. In such cases, the part of the sensor 4 which is inserted into the patient must be sterile and cannot be reused between patients. For example, only the sensor probe 8 comprising the sensing substance 9 may be disposable and not the detector 14 or light source 10.

The analysis system 30 is configured to carry out the method by controlling the sensor 4 and performing processing of signals received from the detector 14. The analysis system 30 may also be configured to calibrate the sensor, and/or derive a measure of concentration of the analyte based on measurements from the sensor 4. The analysis system 30 may be connected to the sensor 4 via a wired connection, for example a serial or Ethernet connection, or another interface type specifically designed for the sensor apparatus. Alternatively a wireless connection, such as BLUETOOTH® or Wi-Fi may be used. The analysis system receives signals output by the detector 14, and may also transmit signals to the sensor 4, for example to control the light source 10.

Figure 4:
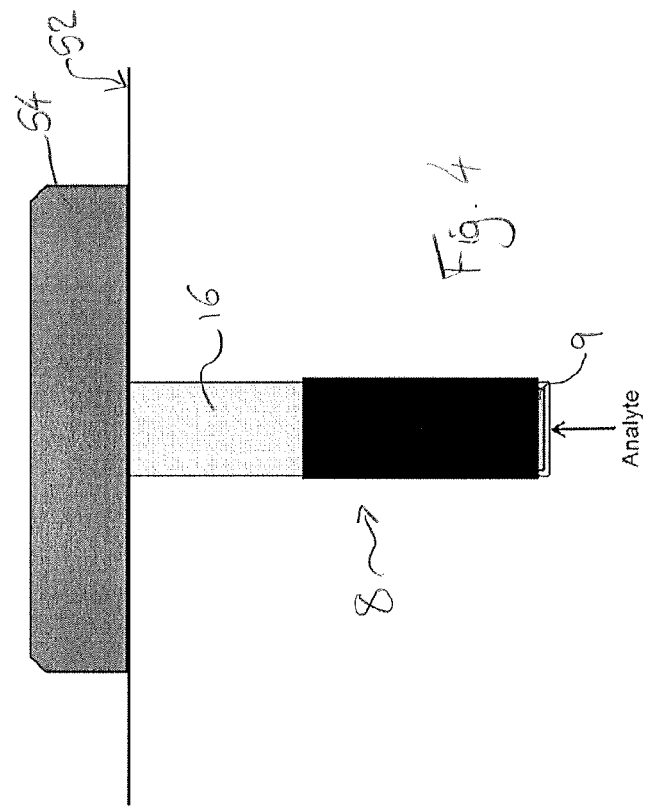
FIG. 4 is a schematic of a possible configuration of a sensor probe for subcutaneous measurement of analyte concentration in blood.
Figure 3:
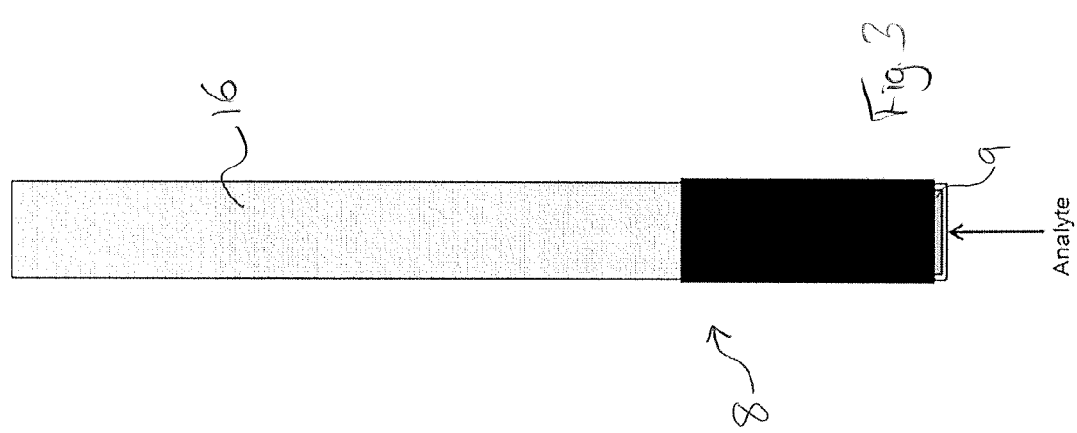
FIG. 3 is a schematic of a possible configuration of a sensor probe for intravascular measurement of analyte concentration in blood.

FIGS. 2 to 4 show specific example embodiments of the sensor 4 for use in clinical contexts and in the case that the sensor 4 comprises a sensor probe 8.

FIG. 2 shows an embodiment in which the sensor 4 is a bypass sensor. Such sensors could be used in an external blood pump to monitor concentrations of analytes in the blood being pumped. Measurements of analyte concentration, in particular oxygen or carbon dioxide, may be used as part of the control of a blood pumping rate by the external blood pump, for example to maintain appropriate levels of oxygenation of blood. In this case, a disposable sensor probe 8 is mounted on a bypass loop 61 such that the sensing substance 9 is exposed to blood passing through the bypass loop. The connector 21 connects the disposable sensor probe 8 to the remainder of the sensor 4. A thermistor or another suitable temperature sensor 20 is mounted within the sensor probe 8 to measure the temperature of the blood.

FIG. 3 shows an embodiment in which the sensor 4 is an intravascular sensor. The sensing substance 9 is located on the tip of the optical fibre 16 that is inserted into the patient via a catheter. The sensor probe 8 contains the fibre optic 16 along with a temperature sensor 20. The sensor probe 8 is connected to the rest of the sensor 4 via the connector 21.

FIG. 4 shows an embodiment in which the sensor 4 is an interstitial sensor. In this case the sensor 4 comprises a sensor probe 8 and an outer part 54. The sensor probe 8 punctures the skin 52 and measures analyte concentrations in interstitial fluid. A retractable needle may be used to puncture the skin 52 and the sensor 4 is connected to the analysis system 30 wirelessly. Alternatively, the analysis system 30 may be disposed in the outer part 54. A temperature sensor is provided to measure the skin temperature. This may be provided within the sensor probe 8 which penetrates the skin 52, or in proximity to the skin 52 within the outer part 54.

The sensing substance 9 may be any suitable substance having an optical property with a spectrum that varies with the concentration of the analyte in the sample, the spectrum having an isosbestic wavelength at which the optical property does not vary with concentration of the analyte. The sensing substance 9 may be provided in the sensor probe 8 immobilised in a polymeric layer. An optical property of the sensing substance 9 may be the absorption strength, and the spectrum may be an absorption spectrum.

In some embodiments, the sensing substance 9 is a luminescent compound. An optical property of a luminescent compound may be the luminescence emission intensity (such as the fluorescence emission intensity or the phosphorescence emission intensity), and the spectrum may be an emission spectrum. Another optical property of a luminescent compound may be its luminescence lifetime (such as the fluorescence lifetime or the phosphorescence lifetime).

In applications where the amount of sensing substance 9 is small, it can be difficult to detect absorption by the sensing substance 9 against the background of excitation light. It is therefore preferred that the sensing substance is a luminescent compound having a luminescent emission spectrum. In particular, it is preferred that the luminescent compound emits light over a range of wavelengths different to the range of wavelengths over which the luminescent compound is excited, as this makes distinguishing between the excitation light and the light emitted from the sensing substance easier.

Where the sensing substance 9 is a luminescent compound, the luminescent emission spectrum may be a fluorescence emission spectrum or a phosphorescence emission spectrum. However, a phosphorescence emission spectrum is typically weaker than a fluorescence emission spectrum as it involves a spin-forbidden transition. In order to provide a sensing substance 9 with a strong optical response to excitation light, it is therefore preferred that the luminescent compound has a fluorescence emission spectrum which varies when the luminescent compound interacts with an analyte.

Accordingly, it is preferred that the sensing substance 9 is a luminescent compound comprising a fluorophore. A fluorophore is a moiety which can absorb light and re-emit light by fluorescent emission. Usually, the fluorophore absorbs light in the visible region of the electromagnetic spectrum. The fluorophore also usually emits light in the visible region of the electromagnetic spectrum. By "the visible region of the electromagnetic spectrum" is meant electromagnetic radiation having a wavelength of from about 400 nm to about 700 nm. The fluorophore may also absorb and/or emit radiation outside the visible region of the electromagnetic spectrum. In a preferred embodiment, therefore, the sensing substance 9 is a luminescent compound comprising a fluorophore, and the fluorescence emission spectrum of the fluorophore varies in the presence of the analyte.

Variation in an optical property of the luminescent compound (such as the emission spectrum of the luminescent compound) is induced by interaction with an analyte. Possible modes of interaction between the analyte and the luminescent compound include:
  protonation of the luminescent compound;
  deprotonation of the luminescent compound;
  collisional quenching of an excited state of the luminescent compound;
  binding to a lone pair of electrons of the luminescent compound; and
  any other non-covalent interaction to facilitate binding.

Other modes of interaction are possible. These interactions will alter the one or more optical properties of the luminescent compound, which may be optically detected.

In some cases, as where the interaction between analyte and luminescent compound involves collisional quenching of the luminescent compound, the analyte does not bind to the luminescent compound. However, in other cases, a chemical bond such as an ionic bond or a covalent bond may be formed between the analyte and the luminescent compound. In such cases, the luminescent compound may comprise a receptor moiety. A receptor moiety is a moiety which can bind to an analyte. It may be preferred that the luminescent compound comprises a receptor moiety, as a receptor moiety typically binds preferentially to the analyte and not to other chemical species. Thus, a luminescent compound comprising a receptor moiety typically generates an optical signal associated specifically with the analyte, which has low susceptibility to interference from other species. A number of examples of luminescent compounds that could be used as the sensing substance 9 for different analytes are provided below for illustrative purposes only.

In an example, the luminescent compound may comprise a moiety of formula (I):

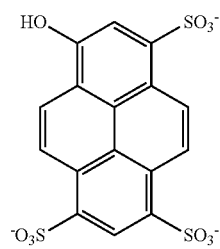

(I)

that is, pyranine, or a derivative thereof. See for instance Ge et al., "High-stability non-invasive autoclavable naked optical CO2 sensor", Biosensors and Bioelectronics, 2003:18: 857-865. This moiety may be attached at any point except the hydroxyl group to the polymer of the polymeric layer. The compound of formula (I) does not comprise a separate receptor and fluorophore; the fluorophore itself acts as the receptor. The moiety of formula (I) can be used to detect acid or $CO_2$, because $CO_2$ forms an acid (carbonic acid) in the presence of water. In the presence of acid (such as carbonic acid formed by $CO_2$), the hydroxyl group of the moiety of formula (I) is protonated. However, as the concentration of acid or $CO_2$ decreases, the hydroxyl moiety becomes deprotonated, leaving a negative charge which is delocalised throughout the fluorophore, changing the fluorescence emission spectrum, and the fluorescence absorption spectrum, of the compound. This change is particularly promoted where the luminescent compound comprising a moiety of formula (I) is immobilised in the polymeric matrix together with a phase transfer agent. An exemplary phase transfer agent is hexadecyltrimethylammonium hydroxide.

A suitable derivative of pyranine which may be used is a moiety of formula (II), below.

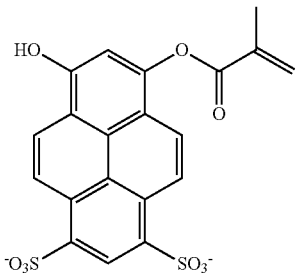

(II)

See for instance Ge et al., "Study on low-cost calibration-free pH sensing with disposable optical sensors", Analytica Chimica Acta, 2012:734:79-87.

In another example, the luminescent compound may comprise a moiety of formula (III):

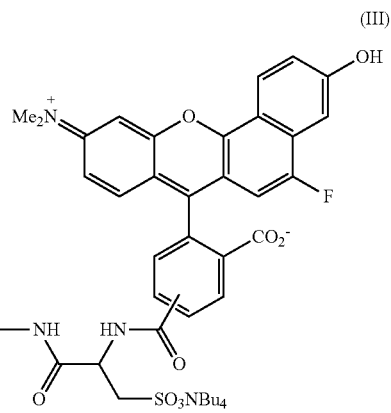

Figure 8:
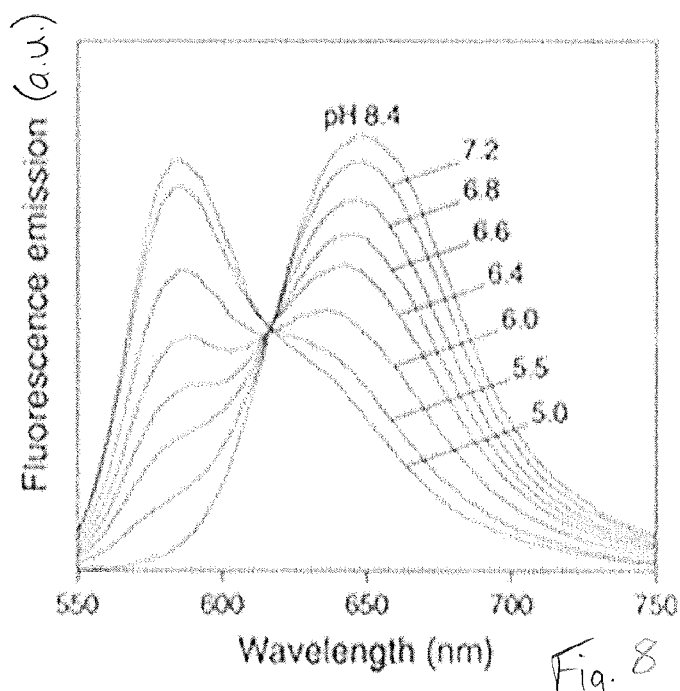
FIG. 8 is a graph of the emission spectrum of a further alternative sensing substance, seminaphtharhodafluor (SNARF®), at different pH values.

(III)

or a derivative thereof. This moiety may be attached at any point to the polymer of the polymeric layer. The compound of formula (III) behaves in a similar way to the moieties of formula (I) and (II): it does not comprise a separate receptor and fluorophore; the fluorophore itself acts as the receptor. In the presence of acid (such as carbonic acid formed by $CO_2$), the hydroxyl group of the moiety of formula (III) is protonated. However, as the concentration of acid or $CO_2$ decreases, the hydroxyl moiety becomes deprotonated, leaving a negative charge which is delocalised throughout the fluorophore, changing the fluorescence emission spectrum, and the fluorescence absorption spectrum, of the compound. The absorbance spectrum of the compound of formula (III) is illustrated in FIG. 8.

Other luminescent compounds are known, and in many cases are commercially available; these compounds may also be used as a luminescent compound. In some embodiments, the sensing substance comprises 8-Hydroxypyrene-1,3,6-trisulfonic acid (HPTS).

A further example of a luminescent compound which can be used to detect acid or $CO_2$ is:

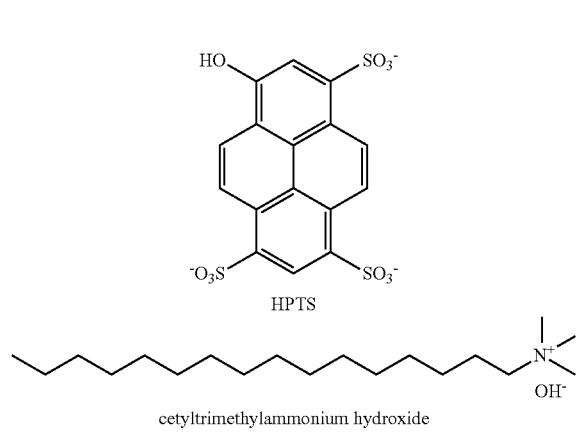

HPTS cetyltrimethylammonium hydroxide

Figure 7:
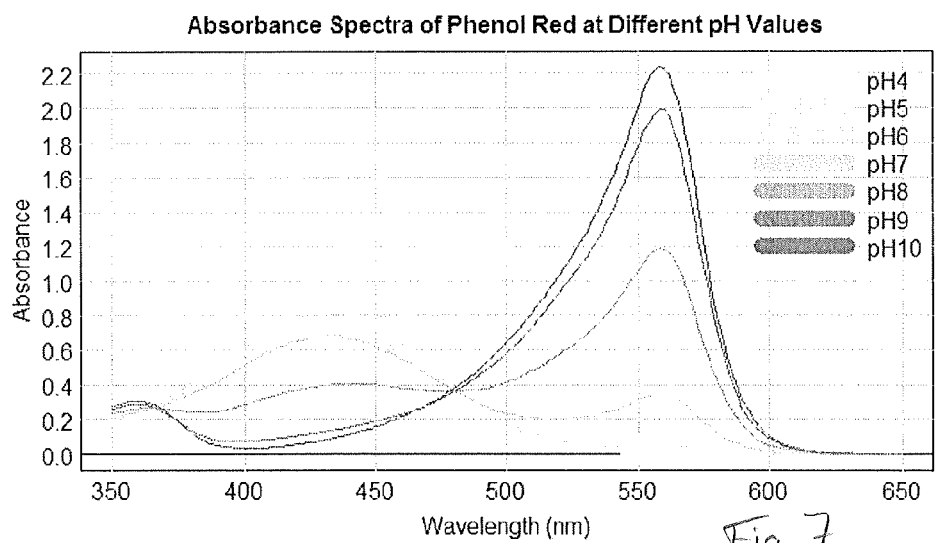
FIG. 7 is a graph of the absorbance spectrum of an alternative sensing substance, phenol red, at different pH values.

The emission and excitation spectra of this luminescent compound are shown in FIG. 7. See for example Ge et al, "High-stability non-invasive autoclavable naked optical CO2 sensor", Biosensors and Bioelectronics, 2003:18:857-865.

A yet further example of a luminescent compound which can be used to detect acid or $CO_2$ is:

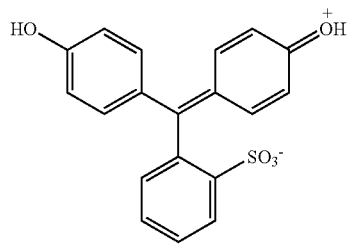

The emission and excitation spectra of this luminescent compound are shown in FIG. 7. See for example Rovati et al, "Plastic Optical Fiber pH Sensor Using a Sol-Gel Sensing Matrix", MOH. YASIN Sulaiman W. Harun and Hamzah AROF, eds. Fiber Optic Sensors.

It will be clear from the above that the sensor 4 may be used for the optical sensing of a variety of analytes. The analyte may be, for example, an ion, a gas, an inorganic compound or an organic compound. The analyte may be present in the sample as a gas, or alternatively it may be dissolved or suspended in another substance, for example a liquid such as interstitial fluid or blood. Where the analyte is an organic compound, it is typically a small organic compound, for example an organic compound comprising fewer than 20 carbon atoms. Particular examples of small organic compounds include saccharides, sugar alcohols, and metabolites such as urea or ketones. Particularly preferred examples of the analyte are $CO_2$, and acid ($H^+$, i.e. a pH sensor).

The methods disclosed herein are directed to validation of a calibration of a sensor 4 (for example, the sensor 4 of FIG. 1) represented by a calibrated relationship between concentration of an analyte in a sample and measurements from the sensor 4 of an optical property of a sensing substance 9. Individual sensors 4 such as those described above will have variations in their manufacture and behaviour that require them to be calibrated before use in order that the values reported by the sensor apparatus are accurate. The calibrated relationship may be determined using a method such as that shown in FIG. 9.

Figures 9, 10:
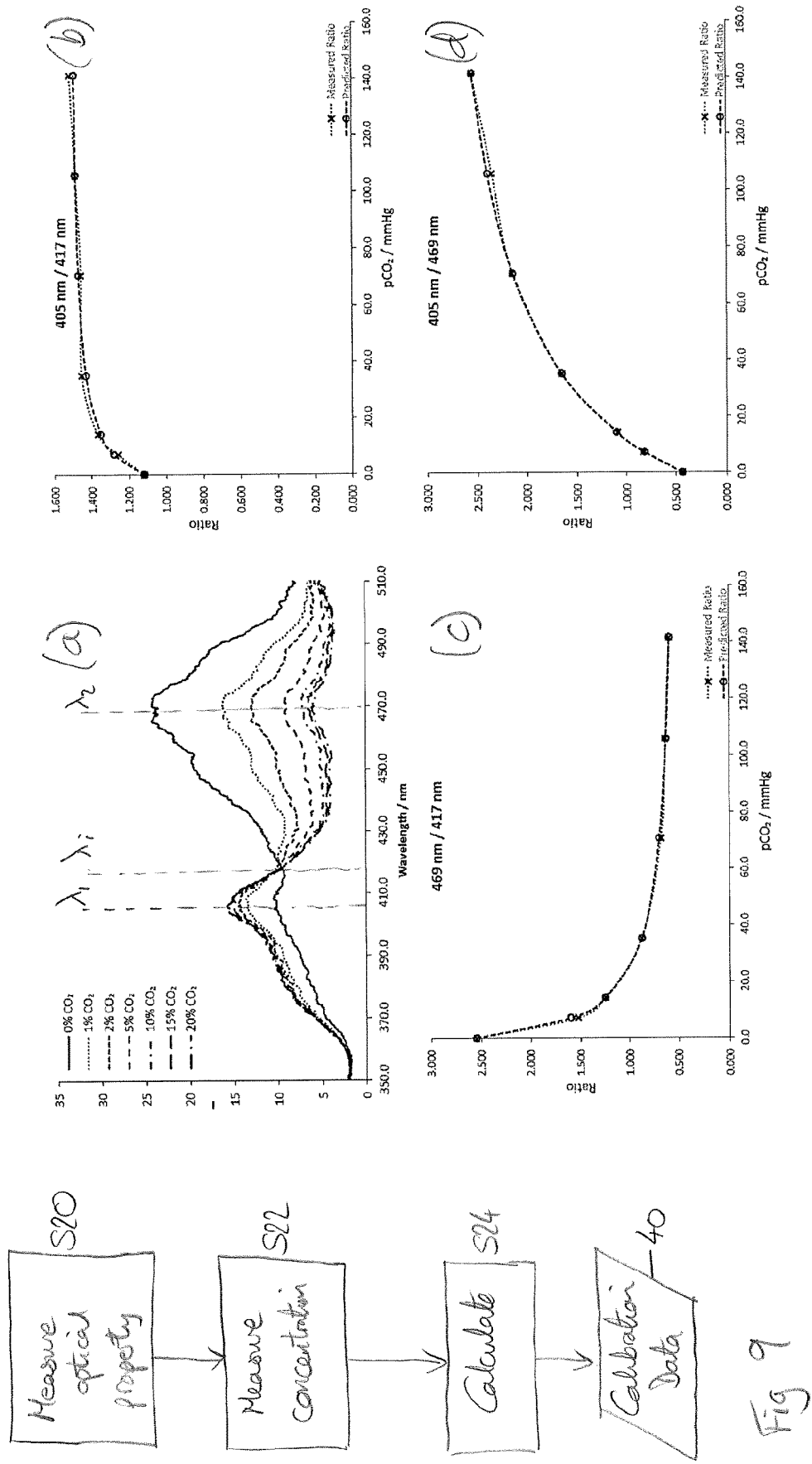
FIG. 9 is a flowchart of a method of determining a calibrated relationship.
FIG. 10 shows graphs of the calibrated relationship between the concentration of an analyte in a sample and ratios of measurements of the optical property made at different wavelengths.

FIG. 9 shows a method of determining the calibrated relationship between the concentration of the analyte and the measurements of the optical property. In step S20, the optical property of the sensing substance 9 is measured while the sensing substance 9 is exposed to the sample containing the analyte, and in step S22 the concentration of the analyte in the sample is measured by an independent method. For example, the sample may be a specially prepared calibration sample, and the concentration of the analyte in the sample may already be known. Alternatively, the sample could subsequently be analysed using another device with a known behaviour to independently determine the concentration of the analyte. Steps S20 and S22 are repeated for a number of different samples with different concentrations of analyte. The number of repetitions required will vary depending on the calibration scheme and the required accuracy. For example, if the variation in the optical property of the sensing substance 9 with the concentration of the analyte is known to follow a particular model, then only a few repetitions may be needed to determine the parameters of the model, where the exact number will depend on the model. Alternatively, if no such model exists, a large number of repetitions may be needed to allow the behaviour at other concentrations to be reliably interpolated from the calibration measurements.

In step S24, the analysis system 30 uses the measured values of the optical property and concentration to determine the calibration of the sensor 4. This may comprise fitting a model to the measurements made in steps S20 and S22 to determine parameters of the model, or may comprises interpolating between the calibration measurements. The output of step S24 is calibration data 40, comprising the calibrated relationship that can be used to determine the concentration of the analyte in new samples from measurements of the optical property of the sensing substance 9 while the sensing substance 9 is exposed to the new sample.

An example of the calibration data 40 is shown in FIG. 10. FIG. 10(a) shows the absorption spectra obtained from a fluorescent carbon dioxide sensor exposed to increasing concentrations of carbon dioxide. The fluorescent output of the luminescent compound 9 was measured at 540 nm when exciting the compound at 3 different excitation wavelengths: 405 nm (where intensity increases with carbon dioxide concentration), 417 nm (the isosbestic point), and 469 nm (where intensity decreases with carbon dioxide concentration). These sets of spectra can be used to define the calibrated relationship in the form of graphs such as those shown in FIGS. 10(b)-(d) for measurements at different wavelengths. FIGS. 10(b)-(d) shows the concentration of analyte as a function of ratios of the measurements of the optical property made at 405 nm, 417 nm and 469 nm in FIG. 10(a), according to the calibrated relationship determined during step S24 of the method of FIG. 9. As will be described later, using the ratio of two measurements at different wavelengths has advantages in some embodiments.

The calibrated relationship defines spectra of the optical property, such as those shown in FIG. 10(a) corresponding to different concentrations of the analyte in the sample. A continuous series of such spectra exist between, above, and below the spectra illustrated in FIG. 10(a) corresponding to other possible values of the concentration, all of which are defined by the calibrated relationship. Thereby, the calibrated relationship relates the concentration of the analyte and the measurements of the optical property. As will be described in further detail below, the methods of validating the calibration disclosed herein comprise making three or more measurements of the optical property. When three measurements are made of the optical property, the calibrated relationship defines a surface in a three-dimensional space, where the dimensions of the space are the possible values of each of the three measurements, and points on the surface represent combinations of the three values which are consistent with the calibrated relationship. Each point on the surface will have an associated value of concentration of the analyte. This can be used to determine if the measurements are consistent with the calibrated relationship.

During continuous operation of the sensor 4, a number of factors can cause drift in the measurements of the optical property. In some embodiments, the light source 10 comprises multiple separate light sources, one for each wavelength at which measurements are made, and any of these light sources may drift in wavelength or intensity subsequent to calibration and induce variations in the measured intensity of light received by the detector. In addition if, after calibration, there is an interferent (either optical or chemical) on either of the two absorbing peaks then these will also cause an apparent change in the intensity. External materials present in the sample that emit fluorescence may also be potential causes of error. During continuous measurement it will be difficult to distinguish between variation in the measurements of the optical property due to error and "true" variation in the measurements due to a change in the concentration of the analyte. The error may mask changes in analyte concentration, or lead to false indications that analyte concentration has changed. This is of critical importance when data is presented to a clinician who will act on that data to administer therapeutics to a patient.

Figure 5:
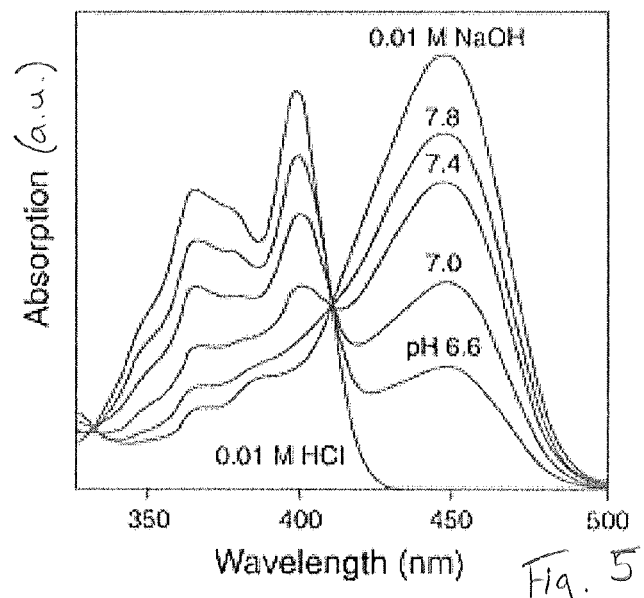
FIG. 5 is a graph of the absorption spectrum of 8-Hydroxypyrene-1,3,6-trisulfonic acid (HPTS) over a range of values of pH.
Figure 12:
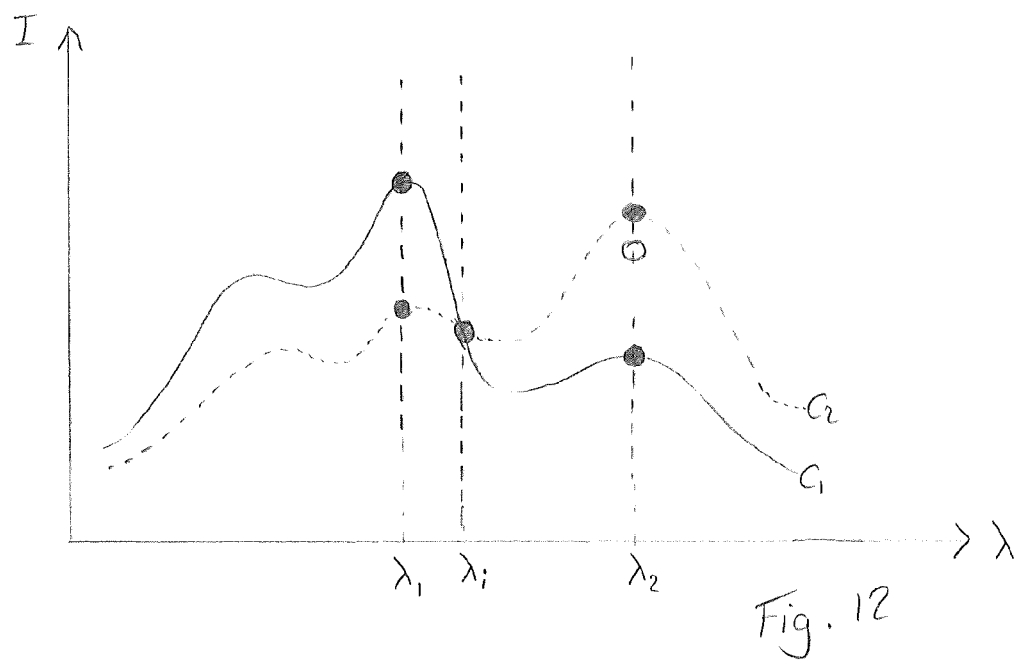
FIG. 12 is a graph illustrating the effect of a change in analyte concentration on measurements of an optical property.
Figure 13:
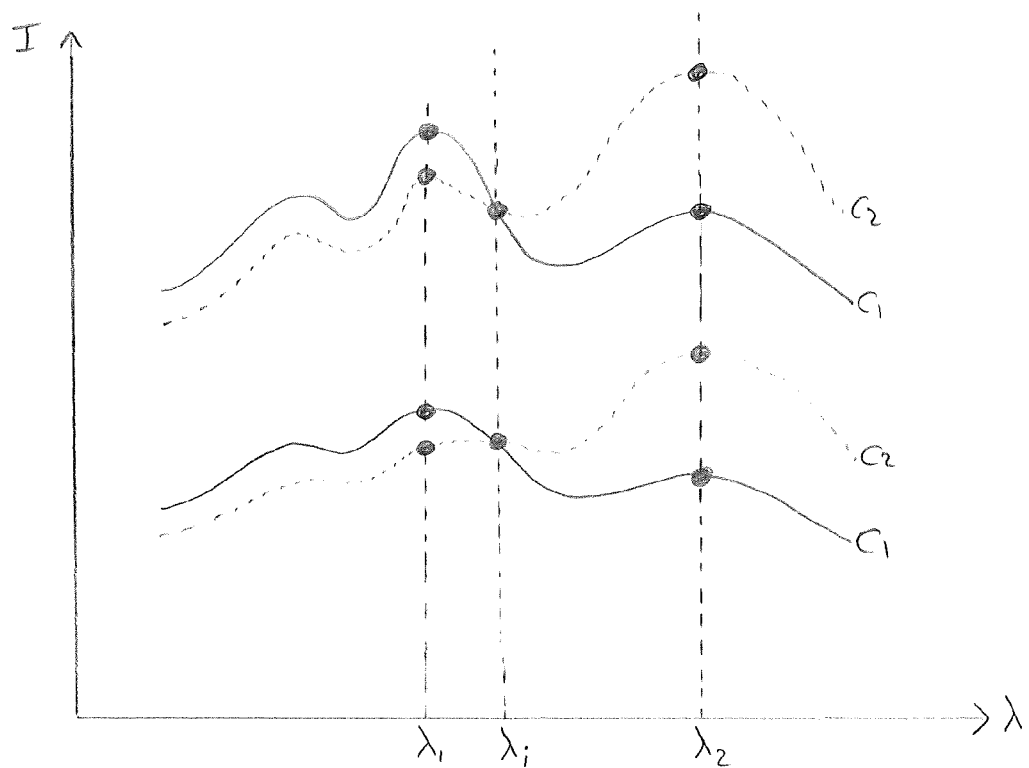
FIG. 13 is a graph illustrating the effect of a uniform drift on measurements of an optical property.

Because the sensing substance 9 has a spectrum with an isosbestic point, this type of error can be detected. At the isosbestic wavelength, the optical property does not vary with concentration of the analyte. In an embodiment, the sensing substance 9 comprises two species in equilibrium, the equilibrium between the two species being dependent on the concentration of the analyte in the sample. This equilibrium gives rise to an isosbestic point. FIG. 5 shows an isosbestic point $A_i$ at 418 nm. This is illustrated schematically by $\lambda_i$ in FIGS. 12 to 14. The isosbestic point is a wavelength at which the absorption of light by the sensing substance 9 comprising the two species remains constant as the equilibrium between the species changes. In the example of FIG. 5, the absorption of light remains constant even when the pH is varied. This can be explained as follows.

The absorbance of the sensing substance is characterised by the Beer-Lambert Law:

$$A = \varepsilon l c \qquad \text{Equation 1}$$

where:
A is the absorption at a particular wavelength;
$\varepsilon$ is the absorptivity or molar attenuation coefficient of the sensing substance at the particular wavelength;
l is the optical path length through the sensing substance; and
c is the concentration of the sensing substance.

The absorbance is determined from the measured intensities using Eq. 2:

$$A = \log_{10} \frac{I_0}{I} \qquad \text{Equation 2}$$

where:
$I_0$ is the intensity of light entering the sensing substance; and
I is the intensity of light leaving the sensing substance.

In the example of FIG. 5, the analytical concentration of the sensing substance 9 is constant in the overall equilibrium so:

$$c_1 + c_2 = c \qquad \text{Equation 3}$$

where $c_1$ and $c_2$ are the concentrations of the two species in equilibrium comprised by the sensing substance 9.

Assuming that the path length is the same for both species, the overall absorbance of the sensing substance at a given wavelength is:

$$A = l(\varepsilon_1 c_1 + \varepsilon_2 c_2) \qquad \text{Equation 4}$$

But at the isosbestic point, the absorptivity of the two species is the same:

$$\varepsilon_1 = \varepsilon_2 = \varepsilon \qquad \text{Equation 5}$$

Hence the absorbance at the isosbestic point is:

$$A_i = l(\varepsilon_1 c_1 + \varepsilon_2 c_2) = l\varepsilon(c_1 + c_2) = l\varepsilon c \qquad \text{Equation 6}$$

Thus, although the absorbance at the isosbestic point does not vary with analyte concentration, it is dependent on the optical path length l, the analytical concentration c of the sensing substance, and the absorptivity of the sensing substance 9 at the isosbestic wavelength. This is also valid in cases where the emission of the sensing substance is measured. The emission of light by each species is proportional to the light absorbed by each species, and so the emission spectrum will show an isosbestic point for equivalent reasons that the absorption spectrum shows an isosbestic point. Due to the presence of the isosbestic point, a change in analyte concentration will cause opposite changes in the optical property at wavelengths above and below the isosbestic point, because a decrease in the concentration of one species causes an increase in the concentration of the other and vice versa. This means it is possible to distinguish between changes due to a change in the analyte concentration, and changes due to error, as will be described further below.

Figure 11:
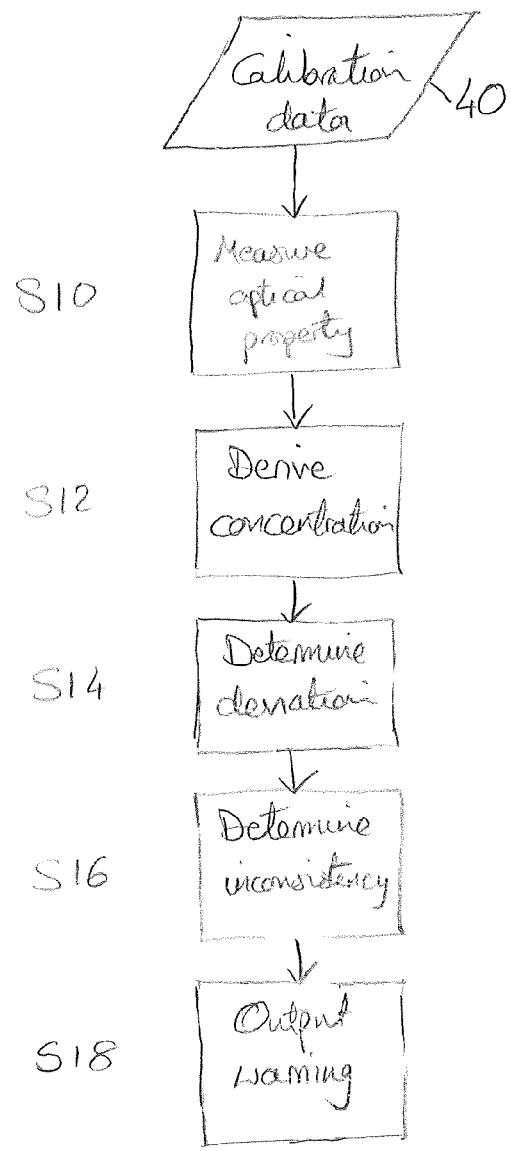
FIG. 11 is a flowchart of a method of validating a calibration of a sensor.

FIG. 11 shows a method of validating a calibration of a sensor that makes use of this insight. The calibration is represented by a calibrated relationship such as that determined using the method of FIG. 9. In an embodiment, the method comprises an initial calibration step of determining the calibrated relationship between the concentration of the analyte and the measurements of the optical property, for example using the method of FIG. 9. The sensor 4 is a sensor 4 such as that shown in FIG. 1 and comprises a detector 14 and a light source 10. The sensor probe 8 comprises a sensing substance 9 such as those described above, and the sensor 4 measures an optical property of the sensing substance 9.

In step S10, the method comprises making measurements of the optical property at three or more wavelengths of light while the sensing substance is exposed to the sample. The measurements made in step S10 may be obtained in different ways, depending in part on the specific choice of sensing substance 9. When the optical property is absorption, step S10 comprises for each one of the three or more wavelengths illuminating the sensing substance 9 using light at the one of the three or more wavelengths, and measuring the intensity of light transmitted by the sensing substance 9 at the one of the three or more wavelengths.

The sensing substance 9 is preferably a luminescent compound, more preferably a fluorescent compound. Sensors 4 comprising a fibre optic 16 have been developed with fluorescent compounds that have a single absorption peak that, when excited with light of a single wavelength, give two overlapping emission peaks with an isosbestic point. In this case the optical property is emission, and step S10 comprises for each one of the three or more wavelengths exciting the sensing substance 9 using light of a first wavelength, and measuring the intensity of light emitted by the sensing substance 9 at the one of the three or more different wavelengths, wherein the first wavelength is the same for each of the three or more wavelengths. This implementation may be preferred in some situations, because only light of a single wavelength is necessary to produce the two overlapping peaks in the emission spectrum. This reduces the complexity of the light source 10, and additionally any variation in the output from the light source 10 will affect both emission peaks equally. This allows the variation to be effectively removed as an error by the ratiometric methodology described further below. However, this type of implementation will require the detector 14 to be able to distinguish between light at different wavelengths.

For other sensing substances, such as HPTS, excitation at different wavelengths results in a single emission peak. For example, the signal from exciting HPTS at 405 nm, 470 nm, and 418 nm results in a single fluorescent emission at 525 nm, as illustrated in FIG. 7. If light at the three wavelengths is provided in temporally separated pulses, then the fluorescent signals from the excitations at the three different wavelengths can be temporally deconvoluted, and the absorption due to excitation at each wavelength determined. In this case, the optical property is absorption, and step S10 comprises for each one of the three or more wavelengths exciting the sensing substance 9 using light at the one of the three or more wavelengths, measuring the intensity of light emitted by the sensing substance 9 at a second wavelength, wherein the second wavelength is the same for each of the three or more wavelengths. This may be preferred where the detector 14 is only able to detect intensity of light, and not wavelength, but will require the light source to be able to emit light at multiple different wavelengths.

In an embodiment, one of the three or more wavelengths is the isosbestic wavelength. As discussed above, the absorbance at the isosbestic point is directly dependent on the optical path length 1, the analytical concentration c of the sensing substance, and the absorptivity of the sensing substance at the isosbestic point. If one of the three or more wavelength is the isosbestic wavelength and the absorbance at the isosbestic point is determined at the point of calibration, then any changes to the path length and analytical concentration of the sensing substance (for example due to photobleaching or chemical interferents) can be directly detected during subsequent use by monitoring the change in the isosbestic point.

In an embodiment, one of the three or more wavelengths is a wavelength at which the spectrum of the optical property of the sensing substance has a maximum or a minimum. The change in the optical property as a function of analyte concentration is largest at the points where the spectrum has a maximum or minimum, and therefore this embodiment further improves contrast. The choice of wavelength may be made by considering where the spectrum has a maximum or minimum at a particular analyte concentration, for example zero.

In an embodiment, step S10 comprises making raw measurements at a plurality of times and time-averaging the raw measurements. Time-averaging raw measurements will reduce the sensitivity of the method to fluctuations or transient changes in the measurements of the optical property, thereby reducing the likelihood of warning signals being falsely generated.

In step S12, the method comprises deriving a plurality of measures of concentration of the analyte in the sample from the measurements at different wavelengths in accordance with the calibrated relationship. The calibration of the sensor 4 provides a relationship between the concentration of the analyte and the measurements of the optical property. In addition, in many systems, concentration values will already need to be calculated for reporting to the user. Therefore, using the concentrations in determining whether the measurements are consistent with the calibrated relationship means no separate comparison using raw measurements is needed. However, in some embodiments, the method may not include a step of calculating concentrations, and the determination of whether the measurements are inconsistent with the calibrated relationship may be made directly on the basis of the measurements of the optical property.

Figure 6:
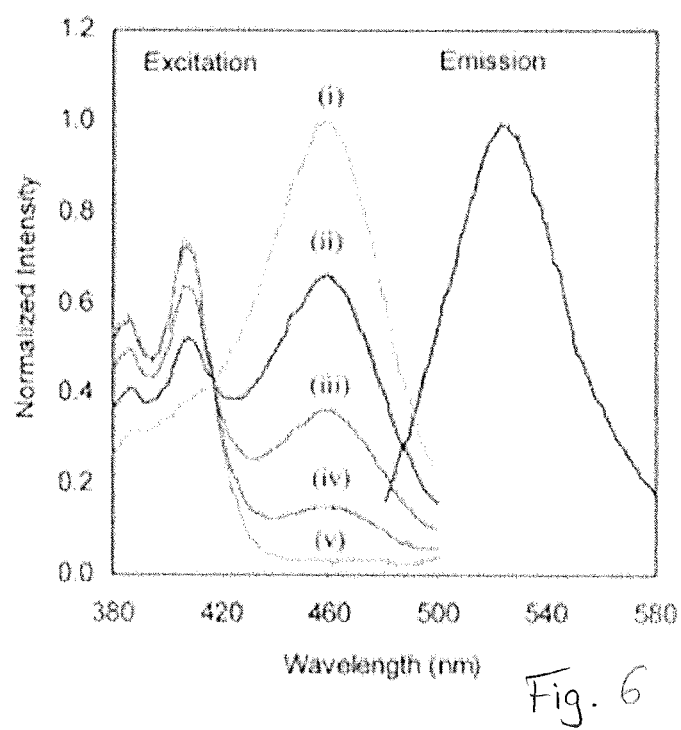
FIG. 6 is a graph showing both the absorption and emission spectra of HPTS at different values of pH.

In step S12, the calibrated relationship comprises a relationship between the concentration and plural ratios between measurements of the optical property at respective pairs of wavelengths, and step S12 comprises calculating ratios between the measurements of the optical property at the respective pairs of wavelengths and deriving the plural measures of concentration from the ratios in accordance with the calibrated relationship. This is advantageous because the plural measures are compensated for certain types of error or drift, and so the sensor 4 does not need to be recalibrated to compensate for these errors. For example, as shown in FIG. 6, the absorption peaks of HPTS are at 405 nm ($A_1$), and 470 nm ($A_2$). Therefore, using Eq. 1 for the ratio of the two peaks shown in FIG. 5:

$$\frac{A_1}{A_2} = \frac{\log_{10} \frac{I_{01}}{I_1}}{\log_{10} \frac{I_{02}}{I_2}} = \frac{\varepsilon_1 l_1 c_1}{\varepsilon_2 l_2 c_2} \qquad \text{Equation 7}$$

The two concentrations $c_1$ and $c_2$ correspond to those of the two species comprised by the sensing substance discussed above, under the assumption that the absorption at each of the two peaks is predominantly due to the species with which that peak is associated. Since the optical path length is the same for the light at both wavelengths (particularly where both are transmitted down the same optical fibre 16), then this term cancels, and the ratio eliminates this potential variable, thereby reducing measurement drift that could be caused by, for example, the path length changing due to temperature-related expansion and contraction of the optical fibre 16. In addition, $I = I_0 10^{-A}$, and so in embodiments where the measurement method is such that the same light source 10 is used to make measurements at both wavelengths, changes in the intensity of the light source 10 $I_0$ will not affect the ratio of the peaks either, because any change in $I_0$ causes a proportional change in I. Therefore, the frequency of recalibration is reduced, and less user time is wasted. The effect of using ratios is demonstrated in FIG. 13. A family of valid spectra of the optical property exists for each value of analyte concentration. The two solid lines illustrate two valid spectra at analyte concentration $C_1$ corresponding to, for example, different values of the path length or incident intensity of light from the light source 10. Similarly, the dotted lines represent two such spectra for analyte concentration $C_2$. As for the spectra at different concentrations, intermediate spectra exist over the full range of values that, for example, the incident intensity may take. However, even when ratios of the measurements are used to derive the plurality of measures of concentration, this does not mean that the calibration relationship will hold during subsequent measurements. Other errors may affect measurements at one of the three or more wavelengths differently from measurements at other wavelengths, and therefore still cause drift. Therefore, there is still a need to validate the calibration even if ratios are used.

In an embodiment, the plurality of measures of concentration comprises a measure calculated using a ratio between two measurements of the optical property not made at the isosbestic wavelength. Because the measurement at the isosbestic wavelength does not change with analyte concentration, using a ratio of two measurements of the optical property not at the isosbestic wavelength will improve the contrast in the ratio as analyte concentration changes, thereby improving the sensitivity of the measure of concentration. In particular, using a ratio between two measurements of the optical property, one of the two measurements being made at a wavelength larger than the isosbestic wavelength, and the other of the two measurements being made at a wavelength smaller than the isosbestic wavelength will provide a greater improvement in contrast.

In step S14, the method comprises determining a measure of deviation of the measurements of the optical property from the calibrated relationship. In the method of FIG. 11, the measure of deviation is a measure of variation between the plurality of measures of concentration calculated in step S12. However, in embodiments which do not include calculating measures of concentration, the measure of deviation may be calculated directly from the measurements of the optical property. A measure of concentration can be determined from each measurement individually, as the measurements at any particular wavelength should have a different value for each concentration of the analyte. Comparing the measures of concentration determined using different ones of the measurements provides a convenient way to determine if the measurements are consistent with the calibrated relationship. Alternatively, in an embodiment where one of the three or more wavelengths is the isosbestic wavelength, the measure of deviation may be a deviation of the measurement of the optical property at the isosbestic wavelength from the measurement of the optical property at the isosbestic wavelength during calibration.

In an embodiment, the measure of variation is a coefficient of variation. Other measures of variation may be used depending on what is most appropriate, for example a range of the measures of concentration, a standard deviation, or similar.

In step S16, the method comprises determining whether the measurements of the optical property are inconsistent with the calibrated relationship. In the method of FIG. 11, the measurements of the optical property are determined to be inconsistent with the calibrated relationship if the measure of deviation determined in step S14 is above a predetermined threshold. If the three or more measurements are consistent with the calibrated relationship, then the plurality of measures of concentration determined in step S14 should be the same. For example, in FIG. 12, the concentration corresponding to the solid dot on the solid line at $\lambda_1$ is the same as the concentration corresponding to the solid dot on the solid line at $\lambda_2$, i.e. $C_1$. However, the concentration corresponding to the open dot at $\lambda_2$ will be a concentration between $C_1$ and $C_2$ where the spectrum of the optical property intersects the open dot. Therefore, the measures of concentration determined from the open and solid dots will be different, indicating that the measurements as a set are inconsistent with the calibrated relationship, and some drift has occurred since calibration. Comparing the measure of deviation to a predetermined threshold is advantageous because it gives a well-defined threshold above which the measurements are considered to be inconsistent, and provides a quantitative measure of how far the measurements have drifted over time. Therefore, the measurements reported by the sensor 4 can continue to be used if it is known that the drift has not yet become large enough to cause a significant error in the reported value, thereby reducing the frequency at which the sensor 4 must be recalibrated.

As described in relation to step S24 of the method of FIG. 9, when three measurements are made of the optical property, the calibrated relationship defines a surface in a three-dimensional space, where the dimensions of the space are the possible values of each of the three measurements, and points on the surface represent combinations of the three values which are consistent with the calibrated relationship. Therefore, more generally, step S16 comprises determining whether the measurements of the optical property define a point in this space which lies on (or sufficiently close to) a point on the surface defined by the calibrated relationship. In an embodiment, the measure of deviation is a measure of the shortest distance of the point defined by the measurements of the optical property from the surface defined by the calibrated relationship. For example, if the measurements of the optical property at the three or more wavelengths (represented by the solid dots) fall on the solid line of FIG. 12, then it can be determined that the concentration of the analyte is $C_1$. If the measurements of the optical property fall on the dotted line, then it can be determined that the concentration of the analyte is $C_2$. However, if the measurements of the optical property at three different wavelengths are given by the solid dots at $A\lambda_1$ and $\lambda_i$, and the open dot at $\lambda_2$, then it can be determined that the three measurements do not fall on any of the spectra defined by the calibration, and the measurements are inconsistent with the calibrated relationship. The determination of whether the measurements are inconsistent with the calibrated relationship may be made in this way directly on the basis of the measurements of the optical property in some embodiments, without calculating measures of concentration.

Figure 14:
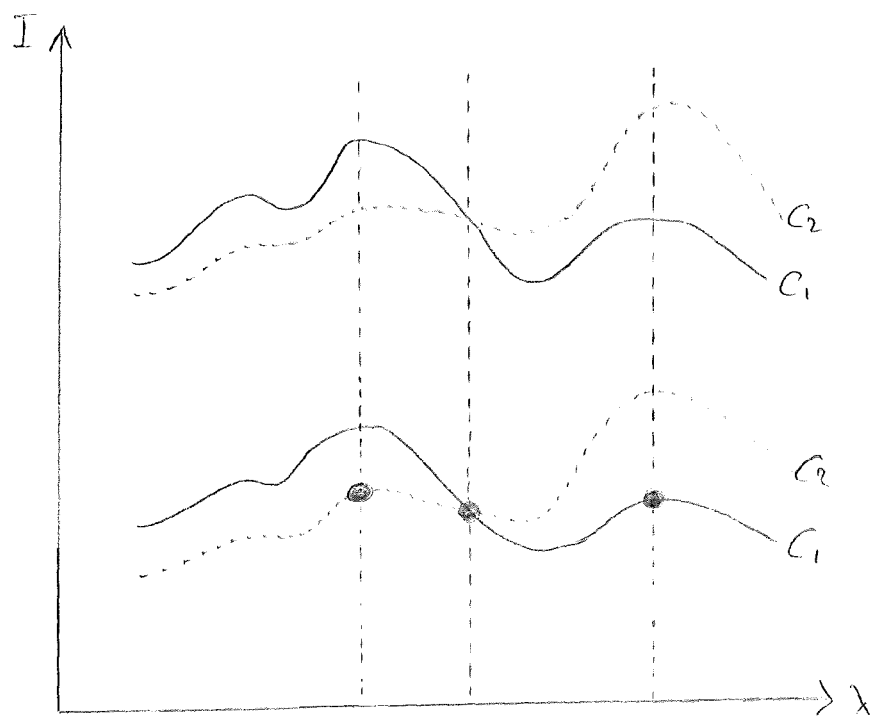
FIG. 14 is a graph illustrating measurements of an optical property which have become inconsistent with the calibrated relationship.

In the method of FIG. 11, the plurality of measures of concentration derived in step S12 are calculated using ratios between measurements at two different wavelengths. The effect of using ratios is demonstrated in FIG. 13. A family of valid spectra of the optical property exists for each value of analyte concentration. The two solid lines illustrate two valid spectra at analyte concentration $C_1$ corresponding to, for example, different values of the path length or incident intensity of light from the light source 10. Similarly, the dotted lines represent two such spectra for analyte concentration $C_2$. As for the spectra at different concentrations, intermediate spectra exist over the full range of values that, for example, the incident intensity may take. If, as shown in FIG. 14, the three measurements are those given by the solid dots, then none of the possible spectra will be consistent with the measurements, and it can be ascertained that the measurements are inconsistent with the calibrated relationship even when the ratiometric scheme is used. Thereby, the determination of inconsistency can be made only for error that cannot be compensated for using the ratio, and the warning signal will only be output if drift occurs that cannot be compensated for. Also, because the absorbance at the isosbestic point is given by:

$$A_i = \log_{10} \frac{I_{0i}}{I_i} \qquad \text{Equation 8}$$

The ratios $$\frac{A_1}{A_i}$$

and $$\frac{A_2}{A_i}$$

when determined at calibration and then continuously measured and compared in-use post calibration will measure the errors generated by the light sources. This is because, as discussed above, the measurement of the optical property at the isosbestic wavelength should only change dependent on factors that cause error, rather than the analyte concentration. Therefore, measurement errors in $A_1$ and $A_2$ may be corrected by utilising the offset determined at $A_3$.

In step S18, the method comprises outputting a warning signal in response to the measurements of the optical property being inconsistent with the calibrated relationship. This alerts the user that the values reported by the sensor apparatus may no longer be relied upon, thereby preventing, for example, clinicians making clinical decisions based on a false understanding of the concentration of a particular substance in the blood of a patient. The warning signal alerts the user that the sensor 4 needs to be recalibrated. Therefore, recalibration is only performed when the sensor 4 has actually drifted sufficiently far to no longer be reporting reliable values. This reduces time wasted performing regular calibrations that may not be necessary. The alerts may be provided in any suitable manner. For example, the alerts may be one or a combination of audible and visual warnings.

In some embodiments, the method may prompt the user to take a confirmatory sample. The measured values of the optical property can then be compared to the predicted values from the calibration constants to calculate a corrective multiplier to apply to each individual measured value, thus correcting the error and allowing monitoring to continue.

The measurements taken during the validation process may be the same measurements as are used to generate the measure of concentration that is reported to the user. Therefore, in an embodiment, the method further comprises deriving a measure of concentration of the analyte in the sample from the measurements in accordance with the calibrated relationship. This allows values to be reported to the user for monitoring or determination of any suitable action. In an embodiment, the measure of concentration reported to the user may be an average of three or more measures of concentration calculated using the three or more measurements of the optical property.

In an embodiment, the calibrated relationship comprises a relationship between the concentration and a ratio between measurements of the optical property at a pair of wavelengths, and the step of deriving the measure of concentration comprises calculating a ratio between the measurements of the optical property at the two wavelengths and deriving the measure of concentration from the ratio in accordance with the calibrated relationship. Using a ratio between measurements to determine the measure of concentration has advantages in compensating for certain types of error, as discussed above. Therefore, it is advantageous to use when reporting values to the user as well. In an embodiment, the measure of concentration comprises a measure calculated using a ratio between two measurements of the optical property not made at the isosbestic wavelength. This increases the contrast of the ratio, thereby improving the sensitivity of the measure of concentration. The measure of concentration reported to the user may be directly that calculated using a ratio between two measurements of the optical property not made at the isosbestic wavelength, or may be an average of a plurality of ratios each calculated using a different pair of the three or more measurements of the optical property.

The invention claimed is:

1. A method of validating a calibration of a sensor represented by a calibrated relationship between concentration of an analyte in a sample and measurements from the sensor of an optical property of a sensing substance, wherein the optical property of the sensing substance has a spectrum that varies with the concentration of the analyte in the sample, and the spectrum has an isosbestic wavelength at which the optical property does not vary with concentration of the analyte, the method comprising:
making measurements of the optical property at three or more wavelengths of light while the sensing substance is exposed to the sample;
determining whether the measurements of the optical property are inconsistent with the calibrated relationship; and
outputting a warning signal in response to the measurements of the optical property being inconsistent with the calibrated relationship.

2. A method according to claim 1, wherein the method further comprises deriving a measure of concentration of the analyte in the sample from the measurements in accordance with the calibrated relationship.

3. A method according to claim 2, wherein
the calibrated relationship comprises a relationship between the concentration and a ratio between measurements of the optical property at a pair of wavelengths, and
the step of deriving the measure of concentration comprises calculating a ratio between the measurements of the optical property at the two wavelengths and deriving the measure of concentration from the ratio in accordance with the calibrated relationship.

4. A method according to claim 3, wherein the measure of concentration comprises a measure calculated using a ratio between two measurements of the optical property not made at the isosbestic wavelength.

5. A method according to claim 1, further comprising:
determining a measure of deviation of the measurements of the optical property from the calibrated relationship; and
determining that the measurements of the optical property are inconsistent with the calibrated relationship if the measure of deviation is above a predetermined threshold.

6. A method according to claim 5, further comprising deriving a plurality of measures of concentration of the analyte in the sample from the measurements at different wavelengths in accordance with the calibrated relationship, wherein the measure of deviation is a measure of variation between the plurality of measures of concentration.

7. A method according to claim 6, wherein
the calibrated relationship comprises a relationship between the concentration and plural ratios between measurements of the optical property at respective pairs of wavelengths, and
the step of deriving a plurality of measures of concentration of the analyte in the sample comprises calculating ratios between the measurements of the optical property at the respective pairs of wavelengths and deriving the plural measures of concentration from the ratios in accordance with the calibrated relationship.

8. A method according to claim 6, wherein the measure of variation is a coefficient of variation.

9. A method according to claim 1, wherein one of the three or more wavelengths is the isosbestic wavelength.

10. A method according to claim 1, wherein one of the three or more wavelengths is a wavelength at which the spectrum of the optical property of the sensing substance has a maximum or a minimum.

11. A method according to claim 1, wherein the optical property is one of absorption and emission, and the spectrum is respectively one of an absorption spectrum and an emission spectrum.

12. A method according to claim 11, wherein the optical property is emission, and making measurements of the optical property at three or more different wavelengths comprises for each one of the three or more wavelengths:
- exciting the sensing substance using light of a first wavelength; and
- measuring the intensity of light emitted by the sensing substance at the one of the three or more different wavelengths,
- wherein the first wavelength is the same for each of the three or more wavelengths.

13. A method according to claim 11, wherein the optical property is absorption, and making a plurality of measurements of the optical property at three or more different wavelengths comprises for each one of the three or more wavelengths:
- exciting the sensing substance using light at the one of the three or more wavelengths;
- measuring the intensity of light emitted by the sensing substance at a second wavelength,
- wherein the second wavelength is the same for each of the three or more wavelengths.

14. A method according to claim 11, wherein the optical property is absorption, and making a plurality of measurements of the optical property at three or more different wavelengths comprises for each one of the three or more wavelengths:
- illuminating the sensing substance using light at the one of the three or more wavelengths; and
- measuring the intensity of light transmitted by the sensing substance at the one of the three or more wavelengths.

15. A method according to claim 1, wherein the sensing substance comprises two species in equilibrium, the equilibrium between the two species being dependent on the concentration of the analyte in the sample.

16. A method according to claim 1, wherein the analyte is one of carbon dioxide, and hydrogen ions.

17. A method according to claim 1, wherein the sample comprises blood or interstitial fluid.

18. A method according to claim 1, wherein the sensing substance comprises a luminescent compound, optionally wherein the luminescent compound is a fluorescent compound.

19. A method according to claim 18, wherein the sensing substance comprises 8-Hydroxypyrene-1,3,6-trisulfonic acid.

20. A method according to claim 1, wherein making the measurements of the optical property comprises making raw measurements at a plurality of times and time-averaging the raw measurements.

21. A method according to claim 1, further comprising an initial calibration step of determining the calibrated relationship between the concentration of the analyte and the measurements of the optical property.

\* \* \* \* \*